(12) United States Patent
Oesch et al.

(10) Patent No.: US 9,089,368 B2
(45) Date of Patent: Jul. 28, 2015

(54) DEVICE FOR MUTUAL POSITIONING OF LONGITUDINAL BUILDING COMPONENTS

(75) Inventors: Marc Oesch, Biberist (CH); Andreas Lanz, Lyss (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2816 days.

(21) Appl. No.: 10/592,207

(22) PCT Filed: Mar. 10, 2004

(86) PCT No.: PCT/CH2004/000139
§ 371 (c)(1),
(2), (4) Date: Jun. 25, 2008

(87) PCT Pub. No.: WO2005/085658
PCT Pub. Date: Sep. 15, 2005

(65) Prior Publication Data
US 2008/0247818 A1 Oct. 9, 2008

(51) Int. Cl.
*E04B 1/26* (2006.01)
*A61B 17/64* (2006.01)
*F16B 2/06* (2006.01)
*F16B 7/04* (2006.01)

(52) U.S. Cl.
CPC ............ *A61B 17/645* (2013.01); *A61B 17/6466* (2013.01); *F16B 2/065* (2013.01); *F16B 7/0433* (2013.01); *Y10T 403/71* (2015.01); *Y10T 403/7129* (2015.01)

(58) Field of Classification Search
CPC .............. A61B 17/6466; Y10T 403/71; Y10T 403/7129
USPC .......... 403/110, 374.3, 374.4, 374.5, 374.21, 403/375, 384, 385, 389, 391, 399, 400, 403/DIG. 8; 600/226, 230; 606/54–59, 96, 606/264, 277, 278, 324; 29/525.01, 525.02, 29/897, 897.31, 897.312
See application file for complete search history.

(56) References Cited

U.S. PATENT DOCUMENTS 24,303 A * 6/1859 Herald ........................ 172/713
2,651,026 A * 9/1953 Roth et al. .................... 439/431

(Continued)

FOREIGN PATENT DOCUMENTS

DE 91 06 772 U1 8/1991
DE 44 31 278 A1 3/1996
EP 0 700 664 A1 3/1996

*Primary Examiner* — Daniel P Stodola
*Assistant Examiner* — Nahid Amiri
(74) *Attorney, Agent, or Firm* — Fay Kaplun & Marcin, LLP

(57) ABSTRACT

The mutual positioning of longitudinal building components includes two clamps routed towards each other about an axis of rotation. Each of the two clamps comprises two limbs defining an opening located therebetween. The opening is selectively narrowed or expanded by elastic deformation of the clamps such that a longitudinal building component which is introduced into the opening of the clamp is prefixed. The two clamps are provided with a bore which is coaxial to the axis of rotation and penetrates the limbs of the clamps. The two clamps are borne on a shaft and blocking means are provided to selectively block the rotatability of the two clamps about the axis of rotation and press the limbs of each clamp against the longitudinal building component inserted into the opening of the clamp. One of the two clamps is S-shaped such that it defines two diametrically opposite clamp openings.

20 Claims, 2 Drawing Sheets

(56) References Cited

U.S. PATENT DOCUMENTS

Figure 1:
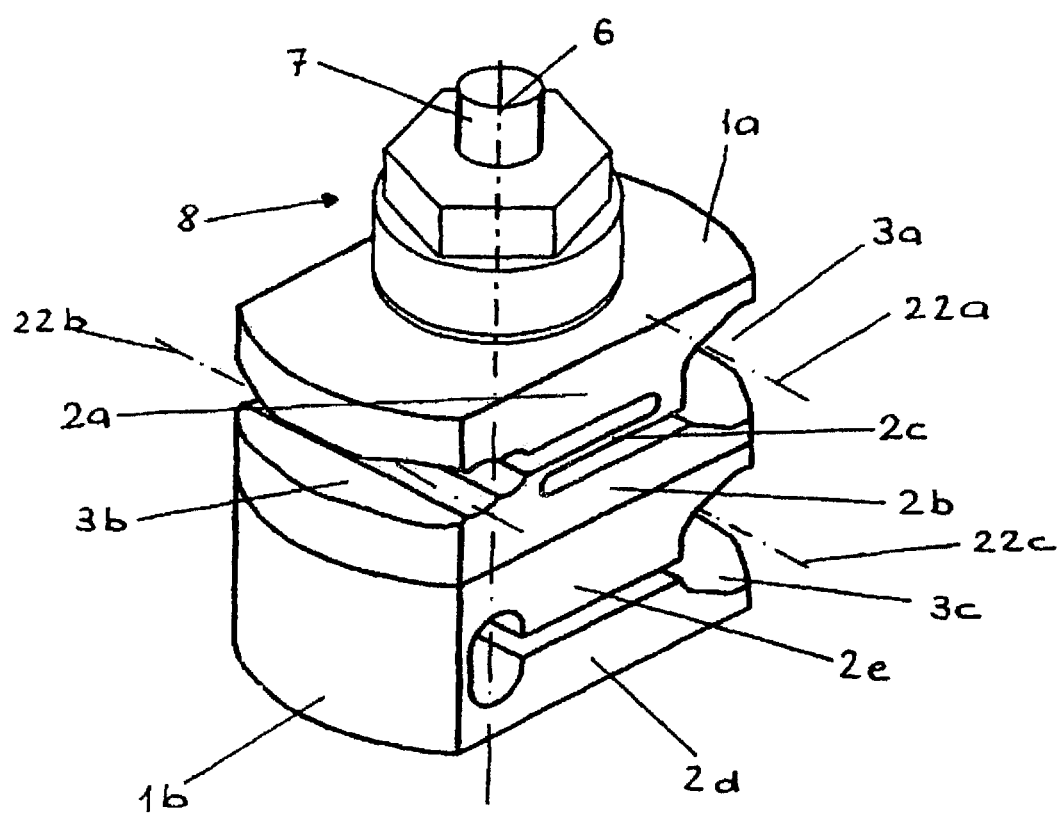

| | | | |
|---|---|---|---|
| 3,651,449 A | 3/1972 | Hall et al. | |
| 4,426,805 A * | 1/1984 | Riead | 43/44.95 |
| 4,526,023 A * | 7/1985 | Babb | 72/116 |
| 4,620,533 A * | 11/1986 | Mears | 606/54 |
| 4,920,959 A | 5/1990 | Witzel et al. | |
| 4,971,038 A * | 11/1990 | Farley | 600/230 |
| 5,030,220 A * | 7/1991 | Howland | 606/261 |
| 5,727,899 A | 3/1998 | Dobrovolny | |
| 5,792,046 A * | 8/1998 | Dobrovolny | 600/234 |
| 5,888,197 A * | 3/1999 | Mulac et al. | 600/234 |
| 6,058,989 A * | 5/2000 | LaGrange et al. | 144/218 |
| 6,080,153 A * | 6/2000 | Mata et al. | 606/54 |
| 6,105,218 A * | 8/2000 | Reekie | 24/518 |
| 6,277,069 B1 * | 8/2001 | Gray | 600/234 |
| 6,340,361 B1 * | 1/2002 | Kraus et al. | 606/59 |
| 6,342,054 B1 | 1/2002 | Mata | |
| 6,616,664 B2 * | 9/2003 | Walulik et al. | 606/57 |
| 6,702,814 B2 * | 3/2004 | Walulik et al. | 606/57 |
| 7,159,626 B2 * | 1/2007 | Biller et al. | 144/176 |
| 2002/0151892 A1 | 10/2002 | Walulik et al. | |

* cited by examiner

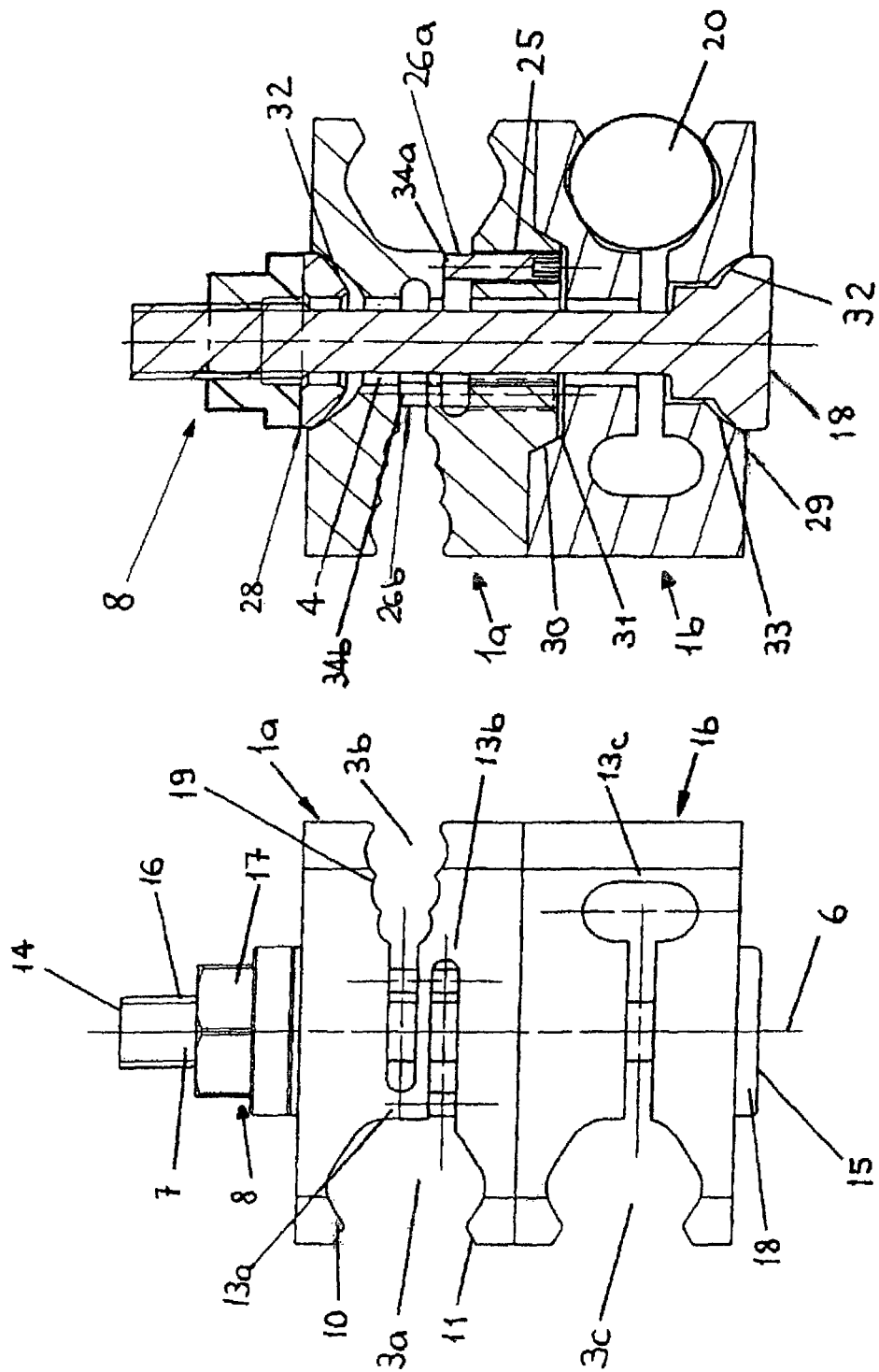

DEVICE FOR MUTUAL POSITIONING OF LONGITUDINAL BUILDING COMPONENTS

Such devices are suitable, in particular, as fastening means for racks, stands, rod constructions, three-dimensional frame constructions, as well as for surgical fixation devices.

The EP-B 0 700 664 discloses a device, for which four separate jaws, mounted on a shaft, define two openings, into which fastening rods or bone pins can be introduced against the force of a spiral spring positioned between the pair of jaws. The large number of individual parts and their slight flexibility or adaptability to the geometry of the building components, which are to be introduced into the openings, is a disadvantage of this known device.

The U.S. Pat. No. 5,727,899 of DOBROVOLNY discloses a device with two clamps, which, however, are not intended for an external fixator. Admittedly, this known device enables a longitudinal carrier to be snapped in latterlly, however, only into one of the two clamps. However, this snapping in does not take place due to the elastic deformation of the clamp, nor does it take place against the pressure of a spring, which is disposed between the two clamps. Instead, this snapping in requires a separate spring, which is disposed in the opening of the clamp. The transitions (fulcri), which act as pivot joints, are mounted between the openings of the clamps and the fastening ends, so that, when the fastening ends are expanded by means of the lever 90, the clamp openings close, clamping the longitudinal carrier located therein. For this purpose, the clamps have an H shape. The fulcri are between the openings of the clamp and the fastening ends. The following are further disadvantages of this known device, a large number of individual parts
a complicated and expensive installation
complicated and difficult cleaning and only rods of a certain diameter can be accommodated.

The US 2002/0151892 of WALULIK ET AL. discloses a generic device. A first embodiment relates to two-piece clamps and a second embodiment relates to elastically deformable clamps, which are constructed in one piece and in such a manner, that they can be pressed together completely coaxially with the central shaft. For this purpose, the clamps are positioned without clearance on the central shaft.

The invention is to provide a remedy here. It is an object of the invention to provide a device for the mutual positioning of the longitudinal building components, which can be constructed simply from a minimum number of individual parts and is very flexible with regard to the building components, which are to be accommodated and positioned opposite to one another.

The advantages, achieved by the invention, are to be seen essentially therein that, due to the S-shaped configuration of at least one of the two clamps, on the one hand cumbersome individual jaws may be omitted and, on the other, a separate, spiral spring, which may jam between the two jaws, becomes unnecessary. In addition, in comparison to the prior art, the inventive construction permits greater flexibility with respect to the building components, which are to be accommodated in the clamp opening and the diameter of which may vary within a larger range. With that, it is possible, with a single device, to position a large number of differently dimensioned building components against one another whereas, in a case of the prior art, the building component and the fastening device must be matched to one another, so that a plurality of differently dimensioned fastening devices is necessary, in order to be able to manage all application cases.

For a special embodiment, at least one of the two clamps has one or more boreholes, which extend parallel to the axis of rotation and in which locking-in-position pins can be moved parallel to the axis of rotation. These locking-in-position pins make it impossible for the clamp openings to be closed only to such an extent that, as a result, the diametrically opposite clamp openings would not be opened once again.

For a further embodiment, the borehole in the two clamps at least partially has a diameter, which is larger than the shaft. By these means, individual clamp limbs can be tilted relative to the shaft, in order to narrow or expand the clamp opening in this way.

In the case of a further embodiment, the clamp limbs are connected in such a manner with one another, that a pliers-like opening and closing of the clamp limbs can be realized about a fulcrum.

Preferably, the clamp is constructed in one piece. The advantages over a 2-piece version lie therein that fewer individual parts are required and that a separate spring element is not necessary, since the clamp is self-springy.

In the case of a further embodiment, the clamp opening has a constriction. As a result, the clamp opening, which is constricted at the outside, can be expanded in one step against the elasticity of the clamp with a longitudinal building component, such as a rod, a longitudinal carrier or a screw, so that the building component can be introduced laterally into the clamp opening. Due to the elasticity of the clamp, the clamp opening, which is expanded on the inside, then closes automatically about the building component that has been introduced and guarantees a primary preliminary fixing of the building component in the clamp opening. In a second step, both clamps can be fixed simultaneously and definitively against one another and with the building component pre-fixed therein.

In the case of a further embodiment, the clamp opening expands towards the outside. With that, the longitudinal building components can be pressed more easily into the clamp opening against the elasticity of the clamp.

For a further embodiment, the clamp openings are constructed channel-like and have a channel axis. At least one of the clamp openings has a cross sectional surface, which is orthogonal to its channel axis and the boundary of which has several circular arcs of different diameter, which are disposed one behind the other at the adjoining clamp limbs. The advantage of this construction lies therein that rods of different external diameters can be clamped fast in these clamp openings.

For a further embodiment, the mutually adjacent clamp limbs of the two clamps comprise a conical elevation and a conical depression respectively, which engage one another and are coaxial with the axis of rotation. By these means, the two conical elements are pressed into one another when the device is blocked, so that, due to the therefrom resulting wedging, rotation about the axis of rotation of the two clamps relative to one another can be prevented. Preferably, the surfaces of the conical elevation and/or of the conical depression are roughened, in order to achieve an intensification therewith of the wedging of the two conical elements preventing the relative rotation of the two clamps. Instead of the roughening, denticulations or conical denticulations at the face surfaces, which can engage one another, are also possible.

In the case of a further embodiment, the shaft in the borehole has clearance, so that an inclination of the clamp limbs with respect to the axis of rotation is not prevented during the clamping of rods by the shaft.

For a further embodiment, the borehole, at its outer outlets, comprises borehole segments, each of which has a concave, spherical zone-like surface, which is concentric with the axis of rotation. Preferably, the shaft has a head of larger diameter with a convex spherical zone-shaped surface, which is complementary to the concave, spherical zone-shaped surface of the borehole segments.

For a further embodiment, the blocking means have an intermediate piece with a convex, spherical zone-shaped surface, which is complementary to the concave, spherical zone-shaped surface of the borehole segments. With that, it is possible to compensate for the obliqueness between the shaft and the borehole.

The invention and further developments of the invention are explained in even greater detail in the following by means of the partly diagrammatic representations of several examples, of which FIG. 1 shows a perspective view of an inventive device, FIG. 2 shows a side view of the device of FIG. 1 and FIG. 3 shows a longitudinal section through a modified, inventive device.

In FIGS. 1 to 3, an embodiment is shown, which comprises two clamps 1a and 1b, which can be rotated against one another about an axis of rotation 6. A borehole 4, which is suitable for accommodating a shaft 7, which can be connected with the blocking means 8, passes coaxially with the axis of rotation through the two clamps 1a and 1b, which can be brought into contact with one another axially. The diameter of the borehole 4 and that of th shaft 7 are such that the shaft 7 has a clearance in the borehole 4.

The upper clamp 1a is S-shaped and has three clamp limbs 2a, 2b, and 2c, which are disposed transversely to the axis of rotation 6 and of which the axially outer clamp limb 2a and the middle clamp limb 2c, as well as the inner clamp limb 2b, which is adjacent to the lower clamp 1b and the middle clamp limb 2c each have an in-between clamp opening 3a; 3b for accommodating a rod 20. The clamp openings 3a; 3b are constructed in the form of channels and have parallel channel axes 22a; 22b, which are orthogonal to the axis of rotation 6.

The lower clamp 1b comprises an axially exterior clamp limb 2d as well as an interior clamp limb 2e, which is adjacent to the upper clamp 1a. The lower clamp 1b has only one clamp opening 3c between the clamp limbs 2d; 2e. This clamp opening 3c also forms a channel, which is suitable for accommodating a rod 20 and has a channel axis 22c, which is orthogonal to the axis of rotation 6.

Each of the clamp openings 3a; 3b; 3c can be expanded or constricted by the elastic deformation of the corresponding clamp 1a; 1b. The elasticity of the clamp limbs 2a, 2b, and 2c is attained by constructing the longitudinal bridges 13a and 13b of the clamp 1a, which hold the clamp limbs 2a, 2b, and 2c together, appropriately thin. The elasticity of the clamp limbs 2d and 2e is attained by constructing the longitudinal bridge 13c of the clamp 1b, which hold the clamp limbs 2d and 2e together, appropriately thin. Moreover, each clamp opening 3a; 3b; 3c has a constriction 10 at its opening, which is remote from the axis of rotation 6. Peripherally, the clamp openings 3a; 3b; 3c are provided with expansions 11 to facilitate the introduction of a rod 20 into the clamp opening 3a; 3b; 3c in question.

As shown in FIG. 2, the shaft 7 has at its first end 14 an outer thread 16, over which a nut 17 can be screwed as blocking means 8. At its second end 15, the shaft 7 has been provided with a head 18, which has a larger diameter and rests on the outer clamp limb 2d of the lower clamp 1b. As it is tightened, the nut 17 is pressed against the outer surface of the outer clamp limb 2a of the first clamp 1a, while the head 18 at the second end 15 of the shaft 7 is pressed against the outer surface of the outer clamp limb 2d of the lower clamp 1b. One of the clamp openings 3b in the upper clamp 1a has a cross sectional surface, which is orthogonal to its channel axis 22b and the boundary of which at each of the clamp limbs 2a; 2c has three circular arcs 19 with different diameters, so that circularly cylindrical rods 20 with different diameters can be accommodated in this clamp opening 3b.

As shown in FIG. 3, the mutually adjacent clamp limbs 2b; 2a of the two clamps 1a; 1b have a mutually engaging conical elevation 30 and conical depression 31, which are coaxial with the axis of rotation 6, respectively. The conical elevation 30 is provided here at the surface of the upper clamp 1a, which adjoins the lower clamp 1b, whereas the conical depression 31, which is complementary thereto, is provided at the surface of the lower clamp 1b adjoining the upper clamp 1a. The mutually contacting surfaces of the conical elevation 30 and the conical depression 31 respectively may be roughened, so that a relative rotation of the two clamps 1a; 1b about the axis of rotation 6 is prevented when the blocking means 8 are tightened. Moreover, at the axially external outlets, the boreholes 4, passing through the two clamps 1a; 1b, comprise borehole segments 29, each of which has a concave, spherical zone-like surface 33. Configured complementarily to these borehole segments 29 is the head 18 at the second end 15 of the shaft 7 as well as an intermediate piece 28, which is disposed coaxially between the nut 17 and the upper clamp 1a, that is, the head 18 has a convex spherical zone-like surface 32 directed towards the lower clamp 1b and the intermediate piece 28 also has a convex, spherical zone-like surface 32, which is directed against the upper clamp 1b.

The locking-in-position pins 26 at the upper clamp 1a are also shown in FIG. 3. These locking-in-position pins 26 can be screwed by means of a threaded connection into boreholes 25, which are parallel to the axis of rotation 6 in the inner clamp limb 2b of the upper clamp 1a and can be adjusted so that they limit the pressing together of the clamp openings 3a; 3b at the upper clamp 1a. For this purpose, the locking-in-position pins 26 are screwed in, until a front end 34a of the first locking-in-position pin 26a is in contact with the surface of the middle clamp limb 2c, which is adjacent to the inner clamp limb 2b, and the front end 34b of the second locking-in-position pin 26b is in contact with the surface of the outer clamp limb 2a, which is adjacent to the middle clamp limb 2c.

The invention claimed is:

1. A clamping device for mutual positioning of elements comprising:
   first and second clamps configured and dimensioned for relative rotation with respect to one another about a first axis of rotation, the first and second clamps each including:
   upper and lower clamping arms defining a clamp opening between the arms, the clamp opening configured and dimensioned to receive a longitudinal element,
   a borehole coaxial with the first axis, the borehole traversing the upper and lower clamping arms;
   a shaft extending through the borehole of the first and second clamps; and
   a locking mechanism configured and dimensioned to (1) prevent relative rotation of the first and second clamps about the first axis and (2) secure the clamping arms against longitudinal elements inserted into the clamp openings, wherein at least one of the first and second clamps has an S-shaped profile defining two diametrically opposed clamp openings.

2. The device of claim 1, wherein at least one of the first and second clamps includes a further borehole extending parallel to the first axis, the further borehole configured and dimensioned to receive a pin moveable in a direction parallel to the first axis of rotation.

3. The device of claim 2, wherein the pin limits relative movement of the upper and lower clamping arms.

4. The device of claim 1, wherein the shaft has a diameter, and the borehole includes a portion having a diameter greater than the diameter of the shaft.

5. The device of claim 1, wherein the clamping arms of at least one of the first and second clamps pivot about a fulcrum.

6. The device of claim 1, wherein at least one of the first and second clamps is formed as one piece.

7. The device of claim 1, wherein each clamp opening includes a structural constriction.

8. The device of claim 1, wherein the upper and lower clamping arms of at least one of the first and second clamps include a surface that tapers to provide a larger clamp opening at a point furthest from the first axis.

9. The device of claim 1, wherein the clamp openings define channel axes, and at least two of the clamping arms of at least one of the first and second clamps includes at least two adjacent, semi-cylindrical arcuate surfaces of different size extending parallel to a channel axis.

10. The device of claim 1, wherein the lower clamping arm of the first clamp is adjacent the upper clamping arm of the second clamp, and the lower clamping arm of the first clamp and the upper clamping arm of the second clamp include complementary conical surfaces that engage one another and are coaxial with the first axis.

11. The device of claim 10, wherein at least one of the complementary conical surfaces is roughened.

12. The device of claim 1, wherein the shaft is at least partially threaded.

13. The device of claim 1, wherein the borehole expands to form at least one concave, semi-spherical surface at a first end of the borehole concentric with the first axis of rotation.

14. The device of claim 13, wherein the shaft includes a head of increased diameter which is complementary to the concave, semi-spherical surface formed by the borehole.

15. A clamp for securing longitudinal elements comprising:
   a substantially S-shaped clamp body including three clamping arms defining two diametrically opposed clamp openings for accommodating the longitudinal building elements, and
   a borehole traversing the three clamping arms along a first axis,
   wherein elastic deformation of the clamp body permits constriction and expansion of the clamp openings.

16. The clamp of claim 15, further comprising a further borehole extending parallel to the first axis, the further borehole configured and dimensioned to receive a pin moveable in a direction parallel to the first axis.

17. The clamp of claim 16, wherein the pin limits relative movement of at least two of the clamping arms.

18. The clamp of claim 15, wherein the clamp openings define channel axes, and at least two of the clamping arms include at least two adjacent, semi-cylindrical arcuate surfaces of different size extending parallel to a channel axis.

19. The clamp of claim 15, wherein at least two of the clamping arms include a surface that tapers to provide a larger clamp opening at a point furthest from the first axis.

20. A method for assembling at least two longitudinal building elements comprising:
   inserting a first longitudinal building element into a clamp opening in a first clamp;
   inserting a second longitudinal building element into a clamp opening in a second clamp, the first and second clamps configured and dimensioned for relative rotation with respect to one another about a first axis of rotation, and each of the first and second clamps including:
      upper and lower clamping arms defining the clamp opening between the arms,
      a borehole coaxial with the first axis, the borehole traversing the upper and lower clamping arms, and
      a shaft extending through the borehole of the first and second clamps;
   adjusting the first and second longitudinal building elements about the first axis of rotation to a desired relative position; and
   engaging a locking mechanism configured and dimensioned to (1) prevent relative rotation of the first and second clamps about the first axis and (2) secure the clamping arms against the longitudinal elements inserted into the clamp openings,
   wherein at least one of the first and second clamps has an S-shaped profile defining two diametrically opposed clamp openings.

* * * * *

UNITED STATES PATENT AND TRADEMARK OFFICE
CERTIFICATE OF CORRECTION

PATENT NO. : 9,089,368 B2
APPLICATION NO. : 10/592207
DATED : July 28, 2015
INVENTOR(S) : Oesch et al.

It is certified that error appears in the above-identified patent and that said Letters Patent is hereby corrected as shown below:

In the claims

Claim 10, Column 5, Line 22:
"of the first clamp is adjacent the upper clamping arm of the" should read "of the first clamp is adjacent to the upper clamping arm of the".

Signed and Sealed this
Twenty-fourth Day of November, 2015

Michelle K. Lee
*Director of the United States Patent and Trademark Office*